United States Patent [19]

Endo et al.

[11] Patent Number: 4,681,764

[45] Date of Patent: Jul. 21, 1987

[54] POROUS AND SPHERICAL CARBONACEOUS PRODUCT

[75] Inventors: Hiroshi Endo, Tokyo; Masao Katoh, Koshigaya; Kuniaki Hino, Tokyo, all of Japan

[73] Assignee: Kureha Kagaku Kogyo Kabushiki Kaisha, Tokyo, Japan

[21] Appl. No.: 755,218

[22] Filed: Jul. 15, 1985

Related U.S. Application Data

[63] Continuation of Ser. No. 402,029, Jul. 26, 1982, abandoned, which is a continuation of Ser. No. 205,901, Nov. 12, 1980, abandoned.

[30] Foreign Application Priority Data

Nov. 22, 1979 [JP] Japan ................................ 54-151645

[51] Int. Cl.$^4$ ..................... A61K 33/44; A61K 31/19; A61K 31/05
[52] U.S. Cl. .................................. 424/125; 514/557; 514/731; 514/893
[58] Field of Search ................... 514/557, 893, 731; 424/125

[56] References Cited

U.S. PATENT DOCUMENTS

| | | | |
|---|---|---|---|
| Re. 29,101 | 1/1977 | Amagi et al. | 423/449 |
| 3,909,449 | 9/1975 | Nagai et al. | 252/422 |
| 3,934,007 | 1/1976 | Gussin | 424/125 |
| 3,937,775 | 2/1976 | Horikiri et al. | 264/29 |
| 3,953,345 | 4/1976 | Saito et al. | 252/423 |
| 4,009,232 | 2/1977 | Shiiki et al. | 264/9 |
| 4,045,368 | 8/1977 | Katori et al. | 252/421 |
| 4,122,169 | 10/1978 | Geils | 424/125 |
| 4,140,652 | 2/1979 | Korshak et al. | 424/125 |

FOREIGN PATENT DOCUMENTS

| | | |
|---|---|---|
| 2413092 | 12/1978 | France . |
| 077295 | 6/1975 | Japan . |
| 104495 | 9/1976 | Japan . |
| 148501 | 12/1977 | Japan . |
| 050088 | 5/1978 | Japan . |
| 763165 | 12/1956 | United Kingdom . |
| 1383085 | 2/1975 | United Kingdom . |

*Primary Examiner*—Johnnie R. Brown
*Assistant Examiner*—John W. Rollins, Jr.
*Attorney, Agent, or Firm*—Wegner & Bretschneider

[57] ABSTRACT

Disclosed herein is a novel porous and spherical carbonaceous product having acidic groups, basic groups, phenolic hydroxyl groups and carboxyl groups as functional groups at the following relationships:

(1) the equivalent ratio of the acidic groups to the basic groups is in the range of 0.40 to 2.5 and (2) the value obtained by subtracting the amount of the carboxyl groups from the sum of the amounts of the basic groups and the phenolic hydroxylic groups is larger than 0.60, wherein the amount of the above-mentioned functional groups is expressed by milliequivalent/g of the product.

The novel porous and spherical carbonaceous product having its groups in the above-mentioned relationships exhibits a specific adsorptive capability in living bodies and particularly useful as a pharmaceutical for treating diseases of the liver and kidney after administered orally.

6 Claims, No Drawings

POROUS AND SPHERICAL CARBONACEOUS PRODUCT

This application is a continuation of U.S. application Ser. No. 402,029, filed July 26, 1982, now abandoned, which is a continuation of U.S. application Ser. No. 205,901, filed Nov. 12, 1980, now abandoned.

BACKGROUND OF THE INVENTION

The present invention relates to a novel porous and spherical carbonaceous product having its functional groups in specified relationships among them, which shows an excellent ability to absorb toxic substances in living bodies.

In recent years, a method of removing toxic substances within the living bodies by a hemodialyzer as an artificial organ has prevailed with the increased cases of disease due to troubles in renal- and hepatic functions.

However, there are demerits in the above-mentioned hemodialyser such as the necessity of skilled specialists for operation of the complicated apparatus of hemodialyzer and the high physical- and mental load onto the patient because it is necessary to take out the patient's blood from his body, as well as the relatively high economic expense.

From the above-mentioned viewpoints, a method of removing the endogeneous toxins formed due to the liver- and kidney diseases within the living body by an internal administration of an orally administered pharmaceutical substance, for instance, oxidized starch, has recently been proposed. However, since the proposed medicine is a kind of reactive substances and although it is able to remove intestinal urea, it cannot remove the essentially endogenous toxins caused by the liver- and kidney diseases such as octopamine, beta-amino-isobutyric acid, dimethylamine, etc. and it has a side-reaction of stimulating the intestinal wall, and according to the above-mentioned reasons, such a medicine is not preferable.

On the other hand, in consideration of the favorable properties of medicinal activated carbon of absorbing various substances and of its safety to living bodies, trials of removal of the endogenous toxins caused by the liver- and kidney diseases with the medicinal activated carbon have been carried out. However, although the medicinal activated carbon is useful as an antidote which adsorbs and removes the gastrointestinal toxic substances taken from mouth, it has a demerit of its insufficient ability to remove the endogenous toxins in the intestines due to the diseases of the liver and kidney. The fact is based on the presence of a substance such as bile acids which coat the surface of active carbon and interfers the activity of the medicinal activated carbon. In addition, the medicinal activated carbon is apt to cause constipation after oral administration, the constipation being said to be particularly dangerous to the patients suffering from the liver- or kidney disease.

The present invention is based on the above-mentioned consideration and the studies of the inventor of the present invention for finding a pharmaceutical substance which is able to remove such endogenous toxins caused by the liver- and kidney diseases when internally administered to the patients suffering from such disease. After having discovered that a porous and spherical carbonaceous product containing specified functional groups in specified mutual relationships exhibits an excellent absorptive effect to the above-mentioned endogenous toxins even in the presence of bile acid within the intestinal tracts with a selectiveness of not absorbing the digestive enzymes in the gastrointestinal tracts without causing any symptoms of constipation, we have attained to the present invention.

DETAILED DESCRIPTION OF THE INVENTION

The first characteristic of the present invention is that the porous and spherical carbonaceous produce of the present invention has, as functional groups, acidic groups, basic groups, phenolic hydroxyl groups and carboxyl groups in the following mutual relationships:

(1) the equivalent ratio of the acidic groups to the basic groups is in the range of 0.40 to 2.5 and (2) the value obtained by subtracting the equivalent of carboxylic groups from the sum of the equivalents of basic groups and phenolic hydroxyl groups is larger than 0.60, that is, when the amounts of the acidic groups, the basic groups, the phenolic hydroxyl groups and the carboxyl groups are represented respectively by A, B, C and D milli-equivalent/g of the material (hereinafter referred to as meq/g). The above-mentioned relationships become as follows:

(1) $A/B = 0.40$ to $2.5$ and (2) $(B+C) - D = 0.60$.

The second characteristic of the present invention is to administer the above-mentioned porous and spherical material of carbonaceous substance orally to the patient in order to remove the endogenous toxins within the patient's body, which are caused by diseases of the liver and/or kidney.

Still more, the third characteristic of the present invention comprises the method for preparing the above-mentioned porous and spherical carbonaceous product comprising the steps of heating a porous and spherical carbonaceous substance at a temperature of 350° to 700° C. in an atmosphere containing 0.5 to 20% by volume of oxygen and then further heating at a temperature of 800° to 1000° C. in an atmosphere inert to carbon.

The porous and spherical carbonaceous product according to the present invention (hereinafter referred to as the present product) contains, as has been stated above, the acidic groups, the basic groups, the phenolic hydroxyl groups and the carboxylic groups as its functional groups in the above-mentioned mutual relationships, and in this point, it can be said that the present product is a novel substance.

The present product contains the above-mentioned functional groups in the respective amounts as are shown below.

Acidic groups: 0.30 to 1.20 meq/g (A meq/g)
Basic groups: 0.20 to 0.70 meq/g (B meq/g)
Phenolic hydroxyl groups: 0.20 to 0.70 meq/g (C meq/g) and
Carboxyl groups: less than 0.15 meq/g (D meq/g).

The above-mentioned contents of the respective functional groups are quantitatively determined as follows:

(a) Acidic group (A group)

After adding one gram of pulverized specimen of the present product passing through Taylor standard sieve of 200 mesh into 50 ml of an aqueous 0.05N NaOH solution and shaking the mixture for 48 hours, the mixture is filtered to remove the specimen and the thus obtained filtrate is titrated to the neutrality. The amount of A groups is represented by the amount of NaOH consumed by the specimen expressed by the unit of meq/g of the specimen.

(b) Basic group (B group)

After adding one gram of pulverized specimen of the present product passing through Taylor standard sieve of 200 mesh into 50 ml of an aqueous 0.05N HCl solution and shaking the mixture for 24 hours, the mixture is filtered to remove the specimen and the thus obtained filtrate is titrated to the neutrality. The amount of B groups is represented by the amount of HCl consumed by the specimen expressed by the unit of meq/g of the specimen.

(c) Phenolic hydroxyl group (C group)

After adding one gram of pulverized specimen of the present product passing through Taylor standard sieve of 200 mesh into 50 ml of an aqueous 0.05N $Na_2CO_3$ solution and shaking the mixture for 24 hours, the mixture is filtered to remove the specimen and the thus obtained filtrate is titrated to the neutrality. The amount of C groups is represented by the balance obtained by subtracting the amount of consumption of $Na_2CO_3$ by the specimen from the amount of acidic groups, expressed by the unit of meq/g of the specimen.

(d) Carboxyl group (D group)

After adding one gram of pulverized specimen of the present product passing through Taylor standard sieve of 200 mesh into 50 ml of an aqueous 0.05N $NaHCO_3$ and shaking the mixture for 24 hours, the mixture is filtered to remove the specimen and the filtrate is titrated to the neutrality. The amount of D groups is represented by the amount of $NaHCO_3$ consumed by the specimen expressed by meq/g of the specimen.

The fact that the specified relationships among the contents of specified functional groups in the present product are specific to the present product will be understood from Table 1 wherein the above-mentioned specified relationships are compared to those of a commercial spherical activated carbon having same shape as the present product.

TABLE 1

| Functional group amounts in meq/g | Porous and spherical carbonaceous product, the product of the present invention | A commercial spherical activated carbon |
| --- | --- | --- |
| Acidic groups (A) | 0.30 to 1.20 | 0.13 |
| Basic groups (B) | 0.20 to 0.70 | 0.44 |
| Phenolic hydroxyl group (C) | 0.20 to 0.70 | 0.13 |
| Carboxyl group (D) | less than 0.15 | 0.001 |
| A/B | 0.40 to 2.5 | 0.3 |
| (B + C) − D | larger than 0.60 | 0.57 |

The present product, that is, the porous and spherical carbonaceous substance according to the present invention preferably consists of porous and spherical particles of 0.05 to 1 mm in diameter, the specific pore volume of the spherical particles of pore radius of less than 80 Å of 0.2 to 1.0 cc/g and the specific pore volume of spherical particles of pore radius of 100 to 75,000 Å of 0.1 to 1.0 cc/g. The specific pore volume of the spherical particles of pore radius of less than 80 Å is determined by a conventional gas adsorption method, and that of pore radius of 100 to 75,000 Å is determined by a mercury porosimeter.

The porous and spherical carbonaceous product according to the present invention, the present product, is produced by the following method:

(a) Preparation of the spherical carbonaceous substance as the precursor of the present product.

A heavy hydrocarbon of a ratio of H/C of 0.45 to 0.80 and of a flow point of 100° to 300° C., in which the presence of unevenly distributed anisotropic regions is not observed under a polarization microscope is used as the starting material. The mixture of this heavy hydrocarbon and an aromatic hydrocarbon such as benzene and naphthalene is dispersed in hot water at a temperature of 100° to 180° C. containing a surfactant while stirring the mixture of the hydrocarbons and hot water to shape minute particles of the mixture of hydrocarbons. After cooling the dispersion to room temperature, the thus formed and solidified minute particles of the mixture of hydrocarbons were separated from the greater part of the aqueous phase by filtration, and the aromatic hydrocarbon contained in the minute particles is removed by extraction with an organic solvent such as hexane, methanol etc. The thus extracted particles are brought into contact with a flow of oxidative gas, for instance an oxygen flow, to effect the oxidation of the minute particles resulting in the content of oxygen in the finished particles of 7 to 25% by weight. Then, the thus partially oxidized minute particles are heated in a flow of a gas having a reactivity to carbon at high temperature such as steam and gaseous carbon dioxide at a temperature of 800° to 1000° C. to convert the particles into the porous and spherical carbonaceous substance.

(b) Production of the present product

The porous and spherical carbonaceous substance obtained as above is heated at a temperature of 350° to 700° C., preferably at 400° to 600° C. in an atmosphere containing 0.5 to 20% by volume of oxygen, preferably 3 to 10% by volume, and then it is further heated at a temperature of 800° to 1000° C. in an atmosphere of a gas inert against carbon, for instance, nitrogen, argon and helium or a mixture of such inert gases to obtain the porous and spherical carbonaceous substance having the afore-mentioned functional groups in the afore-mentioned mutual relationships, that is, the present product.

The atmosphere containing oxygen described above is formed by using oxygen, nitrogen oxides or air as the oxygen source.

A series of the heat-treatments on the porous and spherical carbonaceous substance stated above, confers on the spherical carbonaceous substance a balance between the adsorbency to the acidic and basic substance as well as an adsorbency to the amphoteric substances, and in addition, the series of heat-treatments confer to the porous and spherical carbonaceous substance the selective adsorbing sites expressed by "the equivalent ratio of the acidic groups to the basic groups" and "the value obtained by subtracting the amount of the carboxylic groups from the sum of the amounts of the basic groups and the phenolic hydroxyl groups, (B+C)−D".

The heat-treatment in only an atmosphere containing oxygen may improve the adsorptive ability to basic substance such as amines, however, the adsorptive ability to the amphoteric substance cannot be improved.

The spherical carbonaceous substance, the present product, obtained as above exhibits a specific adsorptive ability to endogeneous toxins within the living bodies, as will be described later, not presumable from the adsorptive ability of the conventional activated carbon, and although the mechanism has not yet been elucidated, the above-mentioned specific adsorptive ability is presumed to be due to the selectivity of the adsorption sites caused by the specified relationships among the various functional groups on the internal surface of the porous and spherical carbonaceous substance, and present product, and the synergestic function of the charged potential on the outer surface and of the minute physical structure of the present product.

In the next place, the application of the pesent product as a medicine for treatment of disease of the liver and/or kidney will be mentioned.

The present product exhibits an adsorptive ability which can never seen in the activated carbon including conventional carbons for pharmaceutical use. That is, the present product exhibits its adsorptive ability to endogenous toxins even in the presence of bile acids, as has been mentioned. In other words, the present product effectively adsorbs octopamine and gamma-aminobutyric acid which are the causal substance of hepatic encephalopathy, endogenous toxins and their precursor in the kidney diseases for example, water-soluble basic and amphoteric substances such as dimethyl-amino beta-amino-isobutyric acid, asparatic acid and arginine.

In addition, as has been mentioned, the present product adsorbs only a little of digestive enzymes within the intestines, which are preferably not to be removed. Moreover, it does not cause constipation after being taken.

Accordingly, the present product works well in the treatment of the tremor and cerebral disorder due to the liver diseases and in the treatment of metabolic abnormality and functional abnormality, and in the improvement of light renal disorder before hemodialysis in the kidney disease and of the conditions during hemodialysis. In addition, it works well in the treatment of other diseases, for example, psychosis due to noxious substances within the living body.

In the cases where the present product is applied as a medicine for treating the diseases of the liver and/or kidney, its dose depends on the object, that is, human or mammals, the age, the personal or individual difference and the disease conditions of the object, and accordingly, an amount over the following range of dose may be administered, however, in human cases, the usual oral dose is 1 to 5 g/day and it is divided into 3 or 4 portions to be taken at a time, 3 to 4 times/day, and according to the conditions, the daily dose is appropriately increased or decreased.

The present product may take optionally any one of several shapes and forms as the medicine to be administered to the patient such as particles, granules, tablets, sugar-coated tablets, capsuled ones, suspension, etc. In the case where it is administered after capsulation, usual gelatin and/or those dissolving within the intestines are possibly used. In cases of using as tablets, it is necessary that the tablets are disintegrated into the original minute spherical particles within the body of the patient. In addition, the present product may be combined with an electrolyte-controlling agent such as aluminum gel and KAYEXALATE®, produced by Winthrop Lab. USA. and administered as a combined medicine.

Since the present product is, as is seen in the following results of toxicological tests, extremely low in toxicity to mammals, it has a medicinal aptitude in addition to the above-mentioned effectiveness as a medicine:

A. Acute toxicity test to mammals:

Each of the porous and spherical carbonaceous substances respectively prepared in Examples 1, 2 and 3 as the present product described later was administered via a stomach tube to each group of male and female JCL-SD rats (average body weight of 87.8±4.3 g of female, and of 97.8±4.0 g of male), a group being consisted of 10 animals of one sex. According to the one-week observation, no death was recorded, and on the autopsy carried out after the end of observation, no abnormal findings were obtained from outside or from internal observation. On several organs as well as no noticeable symptoms of intoxication due to the administration. The respective values of $LD_{50}$ of the present product tested are shown in Table 2.

TABLE 2

| | $LD_{50}$ of the Present Products | | |
|---|---|---|---|
| Specimen | Route of Administration | Sex of rats | $LD_{50}$ (mg/kg) |
| Product of Example 1 | p.o. | Female | over 18,000 |
| | | Male | over 18,000 |
| Product of Example 2 | p.o. | Female | over 18,000 |
| | | Male | over 16,000 |
| Product of Example 3 | p.o. | Female | over 18,000 |
| | | Male | over 16,000 |

B. Sub-acute toxicity test on mammals:

To the respective 10 groups of JCL-SD rats of 4 weeks after birth, five kinds of solid diets were given for one month, each group being consisted of either 10 males or 10 females and the five kinds of solid diets respectively containing 0, 1, 2, 5 and 10% by weight of the present product of example 3. The diet and water were taken ad lib. During the time period of the above-mentioned administration, the amounts of water and the diet taken by the rats and the body weight of the rats were measured, and their behavior was observed.

After the period of administration was over, blood specimens were collected from the rats and then, the rats were sacrificed to be autopsied. The average amount of diets taken by the rats during the period of administration was as follows, respectively corresponding to the content of the present product of 1, 2, 5 and 10% by weight, 1100, 2300, 5700 and 11400 mg/kg body weight of female rat, and 1400, 2800, 7000 and 14000 mg/kg body weight of male rat.

Although a slight suppression of body weight gain was observed in the middle stage of the test on the group of male rats which took the diet of highest content of the present product, the body weight was recovered afterwards. Except for the above-mentioned findings, no noticeable abnormal findings were obtained on body weight gain, the general conditions, blood examination, urinalysis, autopsy, weight of organs and pathohistological examination on various tissues as well as symptoms of intoxication.

The present invention will be more precisely explained as follows while referring to the non-limitative Examples:

EXAMPLE 1

Three hundred grams of a heavy hydrocarbon of H/C of 0.55, a flow point of 220° C., not having localized presence of anisotropic region under a polarization microscope and 100 g of naphthalene were introduced into an autoclave provided with a stirrer, and the mixture was further mixed well at a temperature of 180° C. Into the thus obtained liquid mixture, 1200 g of an aqueous 0.5% solution of polyvinyl alcohol (degree of saponification of 88%) were added. Then, the mixture was vigorously stirred at a temperature of 140° C. for 30 min and cooled to room temperature while stirring to form a dispersion of spherical particles of 0.07 to b 1,2 mm in diameter. After separating the larger part of water from the particles, the spherical particles were treated by hexane in an extractor to remove naphthalene contained in the particles by extraction and dried by air flow. The thus extracted particles were heated to 300° C. at a rate of temperature-raise of 25° C./hour by a flow of heated air in a fluidized bed system and further heated for 2 hours at a fixed temperature of 300° C. to be spherical particles containing 14% by weight of oxygen. The oxygen-containing spherical particles were heated to a temperature of 900° C. by steam in a fluidized bed system and heated for two hours at the same temperature to be porous and spherical carbonaceous particles as the precursor of the present product.

The thus obtained precursor was heated to a temperature of 600° C. in an atmosphere containing 3% by volume of oxygen and further heated for 3 hours in the same atmosphere. Then, the precursor was further heated to a temperature of 950° C. in an atmosphere of nitrogen and kept at the same temperature of 30 min in an atmosphere of nitrogen to be the present product. The properties and the content of various functional groups therein are shown in Table 3.

EXAMPLE 2

Three hundred grams of a heavy hydrocarbon of H/C of 0.65 and of a flow point of 210° C. and 100 g of naphthalene were introduced into an autoclave provided with a stirrer and co-melted by heating to a temperature of 180° C. while stirring. The thus obtained mixed liquid was added with 1200 g of an aqueous 0.5% solution of polyvinyl alcohol of a degree of saponification of 88%, and the mixture was agitated vigorously at a temperature of 130° C. for 30 min. On cooling the mixture to room temperature while stirring, an aqueous dispersion of spherical particles of 0.1 to 1.3 mm in diameter was obtained. After removing a greater part of water from the particles, the spherical particles were treated with hexane in an extractor to remove haphthalene from the spherical particles by extraction. The de-naphthalenized particles were dried by air flow, and heated to a temperature of 300° C. by heated air in a fluidized bed system at a rate of temperature-raise of 25° C./hour, and then further heated for 2 hours at 300° C. to be spherical particles containing 20% by weight of oxygen. The oxygen-containing particles were heated to a temperature of 900° C. in steam by fluidized bed system and kept at 900° C. for 2 hours in steam to be converted into porous and spherical carbonaceous substance as a precursor of the present product. Then, the precursor was kept at a temperature of 450° C. for 4 hours in an atmosphere containing 10% by volume of oxygen and then, it was further heated to a temperature of 800° C. in an atmoshpere of nitrogen and kept at 800° C. for 30 min in the above-mentioned atmosphere to obtain the present product. The adsorbing property and the amount of various functional groups therein are shown in Table 3.

EXAMPLE 3

The oxygen-containing spherical particles of oxygen content of 14% by weight obtained in the course of Example 1 were heated to a temperature of 900° C. in steam by using a fluidized bed system and kept at 900° C. for 2 hours in steam to obtain porous and spherical carbonaceous substance as a precursor of the present product. The precursor was kept at a temperature of 550° C. in an atmosphere containing 3% by volume of oxygen for 5 hours, and then further heated to a temperature of 900° C. in an atmosphere of nitrogen and kept at 900° C. for 30 min in the same atmosphere to obtain the present product. The adsorbing property and the amount of various functional groups therein are shown in Table 2.

Comparative Example

The oxygen-containing (14% by weight) spherical particles obtained in the course of Example 1 were heated to 900° C. in steam by a fluidized bed system and further kept at 900° C. for 2 hours to be converted to porous spherical carbonaceous substance. This substance was further heated at a temperature of 550° C. in an atmosphere containing 3% by volume of oxygen for 5 hours to obtain a porous and spherical carbonaceous substance. The adsorbing property and the amount of various functional groups therein are shown in Table 3.

EXAMPLE 4

In the present Example, the results of determination of the adsorptive property and the content of the specified functional groups of the porous and spherical carbonaceous substances produced in Examples 1 to 3 and Comparative Example, and a commercial spherical activated carbon for use in hemoperfusion are shown. The adsorptive property was determined on beta-amino-isobutyric acid, gamma-aminobutyric acid, dimethylamine and octopamine in the presence of bile acid in vitro, the results also being shown in Table 3. The amount of the above-mentioned adsorbed substance is expressed by the adsorbed amount (mg/g) when the specimen was put into an aqueous solution of the above-mentioned substance at a concentration of 5 mg/dl in the presence of bile acid of a concentration of 0.5% by weight in the aqueous solution.

TABLE 3

Adsorptive Property and Content of Specified Functional Groups of Porous and Spherical Carbonaceous Product

| | Porous and Spherical Carbonaceous Product | | | | |
|---|---|---|---|---|---|
| | Present Product | | | Comparative Instances | |
| | Example 1 | Example 2 | Example 3 | Comparative Example | Commercial Spherical Activated Carbon |
| Adsorptive Property (mg/g) to | | | | | |
| beta-amino-isobutyric acid | 4.5 | 3.9 | 5.0 | less than 0.5 | 0.5 |
| gamma-amino-butyric acid | 3.0 | 2.7 | 4.5 | less than 0.5 | 0.6 |
| dimethylamine | 13.0 | 12.0 | 13.0 | 9.0 | 3.8 |
| octopamine | 100 | 98 | 105 | 100 | 50 |
| Amount of Functional Groups (meg/g) | | | | | |

TABLE 3-continued

Adsorptive Property and Content of Specified Functional Groups of Porous and Spherical Carbonaceous Product

| | Porous and Spherical Carbonaceous Product | | | | |
|---|---|---|---|---|---|
| | Present Product | | | Comparative Instances | |
| | Example 1 | Example 2 | Example 3 | Comparative Example | Commercial Spherical Activated Carbon |
| Acidic group (A) | 0.51 | 0.75 | 0.60 | 1.36 | 0.13 |
| Basic group (B) | 0.42 | 0.33 | 0.39 | 0.14 | 0.44 |
| Phenolic Hydroxyl group (C) | 0.40 | 0.49 | 0.44 | 0.76 | 0.13 |
| Carboxyl group (D) | 0.03 | 0.06 | 0.04 | 0.32 | 0.001 |
| A/B | 1.21 | 2.27 | 1.54 | 9.71 | 0.3 |
| (B + C) − D (meq/g) | 0.79 | 0.76 | 0.79 | 0.58 | 0.57 |

As is seen in Table 3, it is clearly understood that the adsorptive property of the present product, that is the porous and spherical carbonaceous substance having the specified functional groups in the specified mutual relation-ships of the present invention is far superior to that of the product of Comparative Example or the commercial spherical activated carbon hitherto used for hemoperfusion in the treatments of the diseases of the liver and kidney.

EXAMPLE 5

The present Example shows the efficacy of treatment with the present product on the experimental animals suffering from an experimental renel failure.

Three groups of female JCL-SD rats of body weight of 180 to 220 g (a group consisting of 10 animals) were incised transversally of their abdomen under an anesthesia, and the renel hilums of one of the kidneys of each animal was ligated. After suturing the incised part and naturalizing the rat for one week, the same operation was carried out on the other kidney to prepare the groups of rats suffering from experimental renel failure. While giving diet and water taken ad lib, the present product, that is, the porous and spherical carbonaceous substance prepared in Example 3 was forcibly administered to the rats of the first group orally by a stomach tube at a daily dose of 5000 mg/kg, and the product of Comparative Example was administered to the rats of the second group in the same manner as in the first group, the rats of the third group being administered nothing. The state of the rats of the three groups was observed to find the survival period (days) after the second operation. The results are shown in Table 4. As is seen in Table 4, the survival period of the group to which the product of Example 3 was administered was clearly larger than those of the respective groups of rats administered with the product of Comparative Example and administered with nothing, respectively.

TABLE 4

Survival Period of Rats
Unit: day

| Group | Survival Period (average) |
|---|---|
| No. 1 administered with the product of Example 3 | 4.2 |
| No. 2 administered with the product of Comparative Example | 2.8 |
| No. 3 administered with nothing | 2.0 |

EXAMPLE 6

A case of treatment of human renal failure with the present product is shown in the present Example.

The objective patient, a man of 44 in age, suffering from chronic renal failure showed a level of creatinine of 2 to 4 mg/dl for a long time, afterwards a raised level of creatinine of 8 mg/dl after one month and then a still raised level of creatinine of 11 mg/dl after two months accompanied by the subjective symptoms of loss of appetite and fatigues. To the patient at this time, the present product prepared in Example 3 was administered in the capsulated form in gelatin capsules by internal administration at a daily dose of 3 to 4 g for six months.

The level of creatinine of the patient began to show a reduction from after 2 weeks of the commencement of the treatment and was reduced to the stabilized level of 8 to 9 mg/dl together with the substantial disappearance of his subjective symptoms.

EXAMPLE 7

A case of treatment of human liver disease with the present product is shown in the present Example.

A woman of 72 in age suffering from a liver disease, showing a persistent concentration of ammonia in blood of 250 to 300 micrograms/dl and resulting in disturbance of consciousness once a month was treated with the internal administration of the present product produced in Example 3 at a daily dose of 5 g (capsulated in gelatin capsule) for 3 months. During the period of the administration, the disturbance of consciousness never appeared with a reduction of the concentration of ammonia in her blood to 150 micrograms/dl. On suspension of the administration, a light disturbance of consciousness attacked her after 10 days of the suspension with the increased concentration of ammonia in her blood to 200 micrograms/dl. During the period of the administration, the values of examination of her blood and the values of biochemical examination of her blood showed no abnormality.

What is claimed is:

1. A process for producing a porous and spherical carbon product having 0.30 to 1.20 meq/g of said product of acidic groups, 0.20 to 0.70 meq/g of said product of basic groups, 0.20 to 0.70 meq/g of said product of phenolic hydroxyl groups, less than 0.15 meq/g of said product of carboxyl groups, and equivalent ration of 0.40 to 2.5 of said acidic groups to said basic groups and larger than 0.60 meq/g of the value obtained by subtracting the amount of said carboxyl groups from the sum of said basic groups and said phenolic hydroxyl groups, comprising (a) heating a porous and spherical carbon substance having a diameter of 0.05 to 1 mm, a specific pore volume of the spherical particles having a pore radius of less than 80 Å of 0.2 to 1.0 cc/g and a specific pore volume of spherical particles having a pore radius of 100 to 75000 Å of 0.1 to 1.0 cc/g, at a temperature of 350° to 700° C. in an atmosphere containing 0.5 to 20% by volume of oxygen, and (b) heating the treated substance of step (a) at a temperature of 800° to 1000° C. in an atmosphere of a gas inert to carbon.

2. The process of claim 1, wherein said porous and spherical carbon substance is a porous and spherical activated carbon made from a heavy hydrocarbon having a H/C ration of 0.45 to 0.8 and a flow point of 100° to 300° C., in which the presence of an anisotropic region is not observed under a polarization microscope.

3. The process of claim 1, wherein step (a) is carried out at 400° to 600° C. in an atmosphere containing 3 to 10% by volume of oxygen.

4. A porous and spherical carbon product produced by the process of claim 1.

5. A pharmaceutical composition in a dosage unit form for oral administration comprising a porous and spherical carbon product of claim 4 in an amount effective for adsorbing toxic substances within the intestines of humans and mammals and a pharmaceutically acceptable carrier therefor.

6. A method for treating a patient suffering from noxious substances in the gastrointestinal tract which comprises orally administering to said patient the porous and spherical carbon product of claim 4 in an amount effective of adsorbing toxic substances within the intestines of humans and mammals.

* * * * *

UNITED STATES PATENT AND TRADEMARK OFFICE
CERTIFICATE OF CORRECTION

PATENT NO. : 4,681,764
DATED : July 21, 1987
INVENTOR(S) : ENDO et al

It is certified that error appears in the above-identified patent and that said Letters Patent is hereby corrected as shown below:

```
Column 1, line 54, change "interfers" to --interferes--.
Column 2, line 10, change "produce" to --product--.
Column 2, line 23, change "meg/g" to --meq/g--.
Column 5, line 21, change "amino" to --amine-- and
   "asparatic" to --aspartic--.
Column 7, line 1, "b 1,2" to --1.2--.
Column 7, lines 40 to 41, change "haphthalene" to
   --naphthalene--.
Column 8, line 22, change "Table 2" to --Table 3--.
Column 9, lines 32, 36 and 40, change "renel" to --renal--.
Claim 1, line 6, change "and" to --an-- and "ration" to --ratio--.
Claim 2, line 4, change "ration" to --ratio--.
```

Signed and Sealed this

Twelfth Day of April, 1988

Attest:

DONALD J. QUIGG

Attesting Officer

Commissioner of Patents and Trademarks